(12) United States Patent
Murakawa et al.

(10) Patent No.: US 9,236,218 B2
(45) Date of Patent: Jan. 12, 2016

(54) DEFECT INSPECTION APPARATUS AND METHOD USING A PLURALITY OF DETECTORS TO GENERATE A SUBTRACTED IMAGE THAT MAY BE USED TO FORM A SUBTRACTION PROFILE

(71) Applicants: ADVANTEST CORPORATION, Tokyo (JP); TOPPAN PRINTING CO., LTD., Tokyo (JP)

(72) Inventors: Tsutomu Murakawa, Tokyo (JP); Isao Yonekura, Tokyo (JP)

(73) Assignee: Toppan Printing Co., Ltd., Tokyo (JP)

( * ) Notice: Subject to any disclaimer, the term of this patent is extended or adjusted under 35 U.S.C. 154(b) by 38 days.

(21) Appl. No.: 14/254,589

(22) Filed: Apr. 16, 2014

(65) Prior Publication Data
US 2014/0312225 A1 Oct. 23, 2014

(30) Foreign Application Priority Data
Apr. 17, 2013 (JP) ................. 2013-086422

(51) Int. Cl.
*H01J 37/00* (2006.01)
*H01J 37/256* (2006.01)
*G01N 23/225* (2006.01)
*G03F 1/86* (2012.01)

(52) U.S. Cl.
CPC .......... *H01J 37/256* (2013.01); *G01N 23/2251* (2013.01); *G03F 1/86* (2013.01); *H01J 2237/2446* (2013.01); *H01J 2237/24578* (2013.01); *H01J 2237/24592* (2013.01)

(58) Field of Classification Search
CPC .......... H01J 37/44; H01J 37/244; H01J 37/22; H01J 37/266; H01J 37/285; H01J 37/28; H01J 37/268; H01J 37/292; H01J 37/2955; H01J 43/00; H01J 43/007; H01J 43/008; G01Q 30/02
USPC ......................................... 250/306, 307, 311
See application file for complete search history.

(56) References Cited

U.S. PATENT DOCUMENTS

2005/0285034 A1* 12/2005 Tanaka et al. ................. 250/310
2009/0208092 A1*  8/2009 Ominami et al. ............. 382/149
2010/0019148 A1*  1/2010 Nara et al. .................... 250/307
2012/0112066 A1*  5/2012 Ogiso et al. ................... 250/307
2012/0228494 A1*  9/2012 Kuan et al. .................... 250/307

FOREIGN PATENT DOCUMENTS

JP 2012-112927 6/2012

* cited by examiner

*Primary Examiner* — Nicole Ippolito
*Assistant Examiner* — Jason McCormack
(74) *Attorney, Agent, or Firm* — Muramatsu & Associates

(57) ABSTRACT

There is provided a defect inspection apparatus including: an electron scanning unit configured to scan a surface of a sample with an electron beam; a plurality of detectors arranged around an optical axis of the electron beam and configured to detect electrons emitted from the surface of the sample by scanning the electron beam; a signal processing unit configured to generate image data of the surface of the sample based on detection signals from the detectors; an analysis unit configured to detect a defect due to irregularities of the surface of the sample based on the image data; and a control unit configured to control a scanning speed of the electron beam depending on the type of the sample.

8 Claims, 15 Drawing Sheets ch1+ch2+ch3+ch4

(ch1+ch2)−(ch3+ch4)

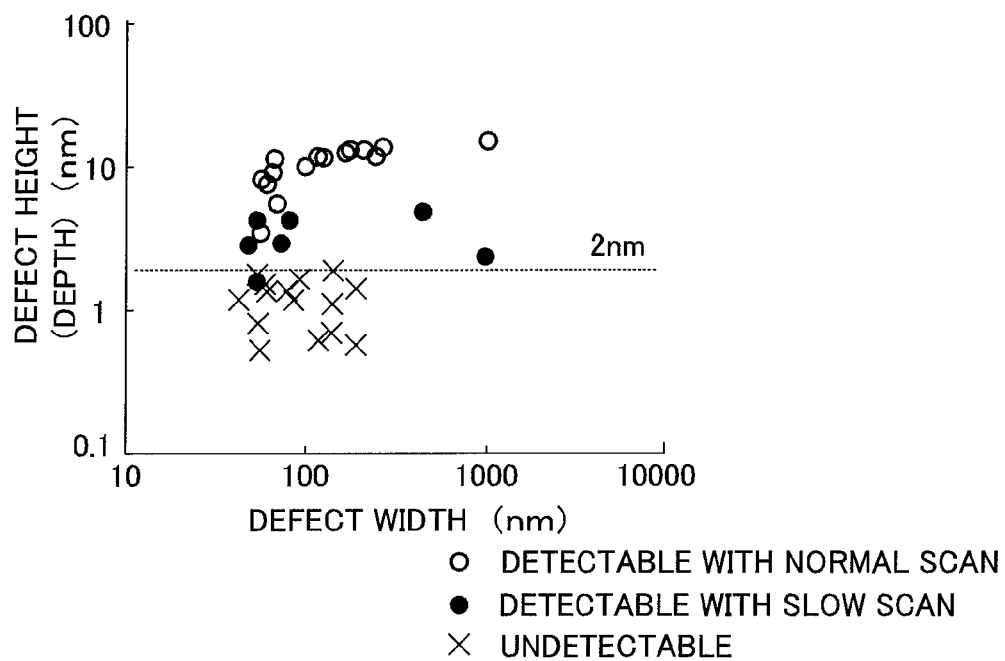

DEFECT INSPECTION APPARATUS AND METHOD USING A PLURALITY OF DETECTORS TO GENERATE A SUBTRACTED IMAGE THAT MAY BE USED TO FORM A SUBTRACTION PROFILE

CROSS-REFERENCE TO RELATED APPLICATIONS

This application is based upon and claims the benefit of priority of the prior Japanese Patent Application No. 2013-086422, filed Apr. 17, 2013, the entire contents of which are incorporated herein by reference.

FIELD

The embodiments discussed herein are related to a defect inspection apparatus and a defect inspection method for inspecting a surface of a sample based on a secondary electron image of the surface of the sample.

BACKGROUND

With the progress of microfabrication of semiconductor devices, an EUV exposure technology using extreme ultraviolet (EUV) light, which has a short wavelength, has been developed. An EUV mask used for the EUV exposure is a light reflective mask, and has a pattern formed of a reflective portion, which reflects light, and an absorption portion, which absorbs light.

If there is a defect arising from irregularities of about several nanometers on a surface of the reflective portion of the EUV mask, the phase of the extreme ultraviolet light at the position is displaced, which may change dimensions or shape of a pattern transferred onto a semiconductor wafer.

Such minute irregularities are difficult to detect by observation using a normal scanning electron microscope (SEM) because the irregularities are buried in noise. For this reason, an atomic force microscope (AFM) is used for inspection of the EUV mask.

Japanese Laid-open Patent Publication No. 2012-112927 shows an example of such defect inspection apparatus and method.

SUMMARY

Problems to be Solved by the Invention

However, the observation using the atomic force microscope has a problem that the observation of a sample takes a long time because a probe mechanically scans the surface of the sample.

In view of this, an object of the present invention is to provide a defect inspection apparatus and a defect inspection method suitable for inspecting a defect arising from minute irregularities.

Means for Solving the Problem

According to an aspect of the disclosure described below, there is provided a defect inspection apparatus including: an electron scanning unit configured to scan a surface of a sample with an electron beam; a plurality of detectors arranged around an optical axis of the electron beam and configured to detect electrons emitted from the surface of the sample by the scanning of the electron beam; a signal processing unit configured to generate image data of the surface of the sample based on detection signals from the detectors; an analysis unit configured to detect a defect due to irregularities of the surface of the sample based on the image data; and a control unit configured to control a scanning speed of the electron beam depending on the type of the sample.

In the defect inspection apparatus of the above-described aspect, when a sample is a reflective mask formed of a conductive material, the scanning speed of the electron beam may be set lower than the scanning speed used when the sample is a transmissive mask with a pattern formed on a substrate formed of an insulating material.

In addition, according to another aspect of the disclosure, there is provided a defect inspection method using a defect inspection apparatus including an electron scanning unit configured to scan a surface of a sample with an electron beam, a plurality of detectors arranged around an optical axis of the electron beam and configured to detect electrons emitted from the surface of the sample by irradiation with the electron beam, and a control unit configured to control the electron scanning unit, the method including the steps of: determining a scanning speed of the electron beam depending on the type of the sample; scanning the electron beam and acquiring a plurality of image data of the surface of the sample captured in different directions based on detection signals of the detectors; generating a subtracted image by finding a difference between image data captured in two opposite directions with an optical axis of the electron beam in between; and extracting a subtraction profile from the subtracted image and detecting irregularities of the surface of the sample based on the subtraction profile.

Effect of the Invention

In the defect inspection apparatus and the defect inspection method of the above-described aspects, the scanning speed of the electron beam is controlled depending on the type of the sample. For example, in the case when the sample is a reflective mask which is formed of a conductive material and tends not to cause a charge-up phenomenon, noise can be suppressed by reducing the scanning speed.

In this way, minute irregularities formed on the surface of the reflective mask can be detected.

BRIEF DESCRIPTION OF THE DRAWINGS

FIG. 8A is a diagram showing a line profile of a projection having a height of 2 nm, and FIG. 8B is a diagram showing a line profile of a projection having a height of 1 nm;

DESCRIPTION OF EMBODIMENT

Figure 1:
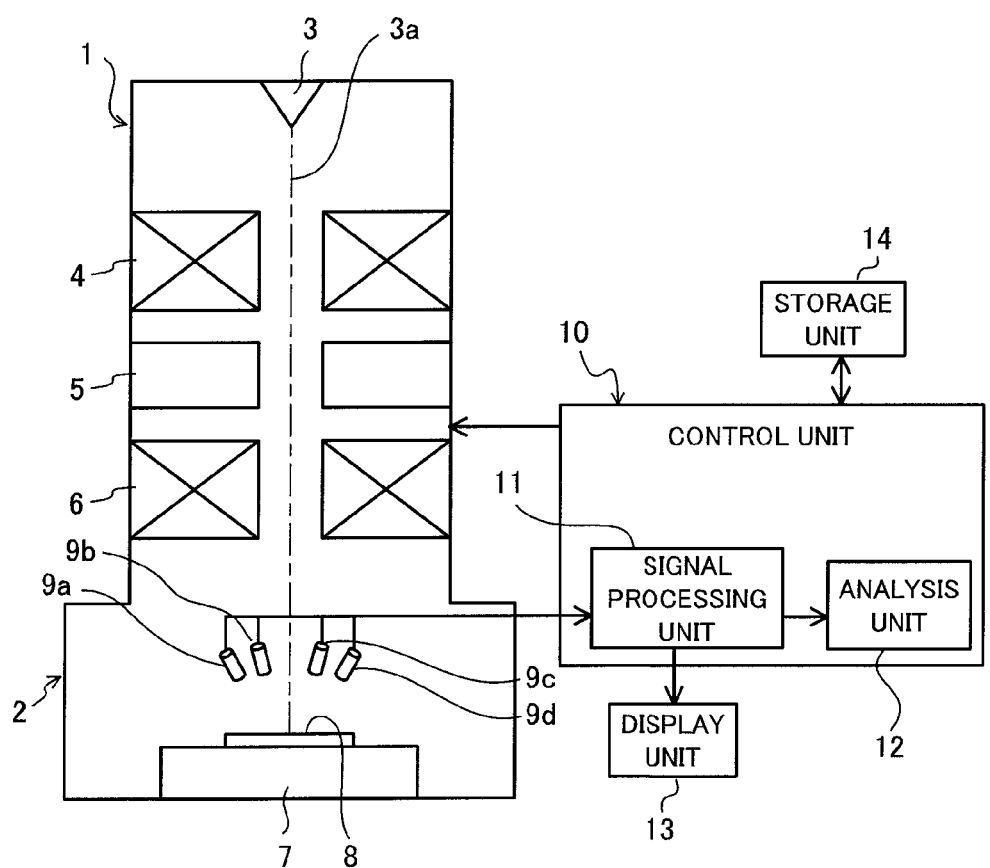
FIG. 1, is a block diagram of a scanning electron microscope (defect inspection apparatus) according to an embodiment.

FIG. 1 is a block diagram of a defect inspection apparatus according to an embodiment.

A defect inspection apparatus (scanning electron microscope) 100 shown in FIG. 1 includes an electron scanning unit 1 configured to irradiate an electron beam 3a on a sample 8, a chamber 2 configured to hold the sample 8, and a control unit 10 configured to control components of the electron scanning unit 1.

The electron scanning unit 1 includes an electron gun 3, and emits electrons from the electron gun 3 at a predetermined acceleration voltage. The electrons emitted from the electron gun 3 are converged by a condenser lens 4 into a primary electron beam 3a. The electron beam 3a The electron beam 3a. The electron beam 3a is deflected by a deflection coil 5, and is then focused by an objective lens 6, so that a surface of the sample 8 is irradiated with the electron beam 3a.

The electron scanning unit 1 scans an observation region on the surface of the sample 8 with the electron beam 3a deflected by the deflection coil 5.

Irradiation with the primary electron beam 3a causes secondary electrons to be emitted from the surface of the sample 8. The secondary electrons thus emitted are detected by a plurality of detectors 9a to 9d provided above a sample stage 7.

Figure 2:
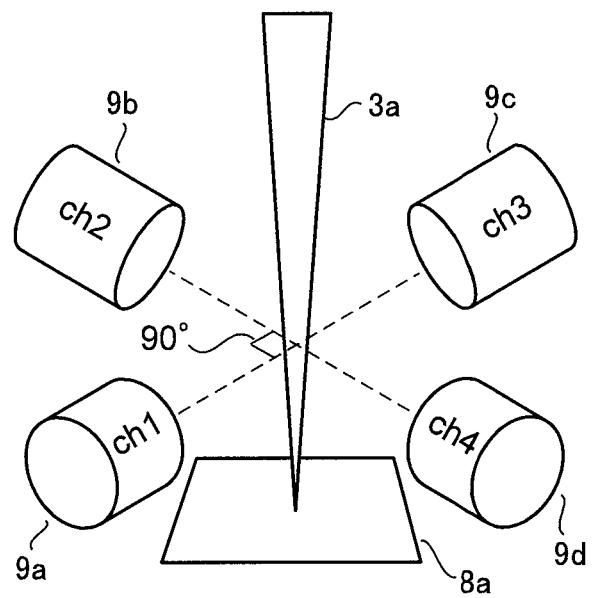
FIG. 2 is a perspective view showing an arrangement of detectors in FIG. 1.

FIG. 2 is a perspective view showing an arrangement of the detectors 9a to 9d.

In the embodiment, as shown in FIG. 2, four detectors 9a to 9d are arranged at equal angles (90°) around an optical axis of the electron beam 3a. In the embodiment, although not limited thereto, the respective detectors 9a to 9d are arranged in the diagonal directions of a rectangular observation region 8a. Note that the number of the detectors is not particularly limited to four.

The detectors 9a to 9d output the amounts of detected secondary electrons to a signal processing unit 11 (see FIG. 1) as detection signals ch1 to ch4, respectively.

The signal processing unit 11 in FIG. 1 converts the amount of secondary electrons detected by each of the detectors 9a to 9d to a digital value with an AD converter. The signal processing unit 11 then associates and arranges the amount of secondary electrons with a position of the primary electron beam 3a deflected by the deflection coil 5 on a two-dimensional array, thereby generating image data (SEM image).

The signal processing unit 11 generates images based on the respective detection signals ch1 to ch4 from the detectors 9a to 9d arranged in different directions. These images reflect the amounts of secondary electrons emitted toward the respective detectors 9a to 9d, and have different luminance values depending on directions of edges of a pattern formed on the surface of the sample 8.

In other words, the luminance value of an edge facing toward a detector is expressed by a higher luminance while the luminance value of an edge facing away from the detector is expressed by a lower luminance.

In addition, the signal processing unit 11 generates image data (SEM image) in an intermediate direction between each adjacent two of the detectors 9a to 9d by adding signals from the adjacent two detectors. For example, the signal processing unit 11 adds the detection signal ch1 and the detection signal ch2 in FIG. 2 with equal weightings, thereby virtually generating image data based on a detection signal of a detector arranged in the intermediate direction (the leftward direction in FIG. 2) between the detector 9a and the detector 9b. In the same manner, the signal processing unit 11 generates image data of the observation region 8a in FIG. 2, which are captured from respective upward, rightward, and downward directions.

Moreover, the signal processing unit 11 generates a full added image by adding all the detection signals ch1 to ch4. This full added image is the same as an image of a SEM image which is obtained by a general scanning electron microscope having only one detector, and accordingly, a difference in luminance due to directions of edges hardly appears in the full added image.

The image data generated by the signal processing unit 11 is stored in a storage unit 14 shown in FIG. 1, and some of the images are displayed on a display unit 13.

The control unit 10 transmits a control signal to the electron scanning unit 1, and controls the acceleration voltage, the current value, and the scanning speed of the electron beam 3a of the electron scanning unit 1.

The control unit 10 includes an analysis unit 12 along with the signal processing unit 11.

The analysis unit 12 extracts image data of the observation region 8a captured from a various directions, and generates a subtracted image from the extracted image data. In addition, the analysis unit 12 obtains a distribution of luminance values (line profile) in a predetermined direction from the subtracted image, and integrates the line profile to obtain an integral profile representing the height of the surface of the sample. The analysis unit 12 then detects irregularities (defect) of the observation region 8a and measures the width and the height (depth) of the defect based on the integral profile.

Next, a method of observing a mask for photolithography using the defect inspection apparatus 100 in FIG. 1 will be described.

Figure 3A:
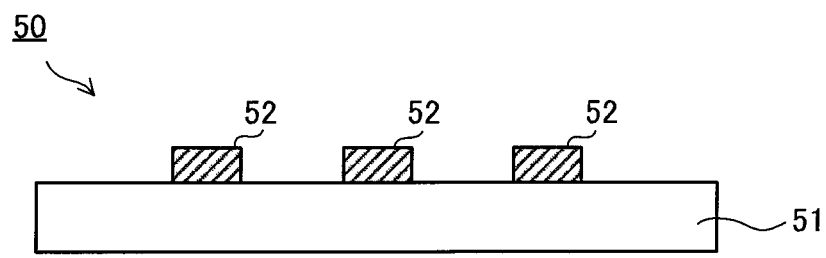
FIG. 3A is a cross-sectional view showing a structure of a transmissive mask and FIG. 3B is a cross-sectional view showing a structure of a reflective mask used for EUV exposure.

FIG. 3A is a cross-sectional view of a transmissive mask.

A transmissive mask 50 shown in FIG. 3A includes a pattern 52 made of chromium or the like on a transparent substrate 51 of silica glass or the like. The mask is used for exposure using visible light or ultraviolet light in particular, and an electronic circuit pattern is transferred by ultraviolet light which has passed through a portion of the substrate 51 where no pattern 52 is formed.

When observing such transmissive mask 50 using the defect inspection apparatus 100, the irradiation amount of an electron beam needs to be reduced to prevent electrification on the surface of the substrate 51 made of an insulating material. For this reason, in the observation of the transmissive mask 50, the scanning speed of the electron beam is relatively high, for example, about 20 MHz.

Figure 3B:
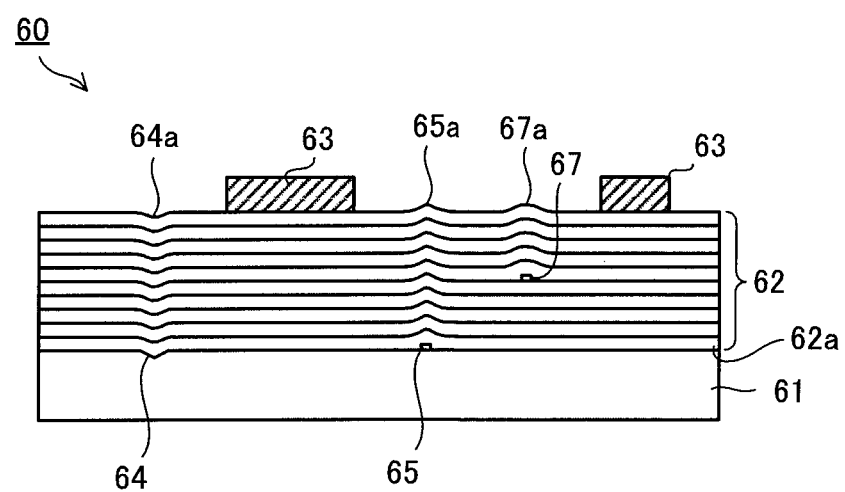

On the other hand, FIG. 3B is a cross-sectional view of a reflective mask used for EUV exposure.

A reflective mask 60 used for EUV exposure in FIG. 3B includes a multi-layer reflective film 62, which is formed by stacking a plurality of reflective films 62a on a substrate 61. A pattern 63 made of a material which absorbs extreme ultraviolet light is formed on the multi-layer reflective film 62.

Each of the reflective films 62a constituting the multi-layer reflective film 62 is a thin film having a thickness of a fraction of the wavelength of the extreme ultraviolet (EUV) light (for example, about 13 nm). If a recess 64 and foreign materials 65, 67 exist on the surface of the substrate, a recess-shaped pit defect 64a and projection-shaped bump defects 65a, 67a remain above the recess 64 and the foreign materials 65, 67.

If such minute pit defect 64a and bump defects 65a, 67a each with a height (or a depth) of about several nanometers exist, the phase of the extreme ultraviolet light reflected at these portions is displaced, which may cause deformation or discrepancy in line width of a transferred pattern.

In view of this, in the embodiment, with a focus on the fact that the multi-layer reflective film 62 of the EUV mask 60 is made of a conductive material, such as a mental, and thus tends not to cause a charge-up phenomenon, a surface of a sample is observed with a reduced scanning speed of an electron beam.

Figure 4A:
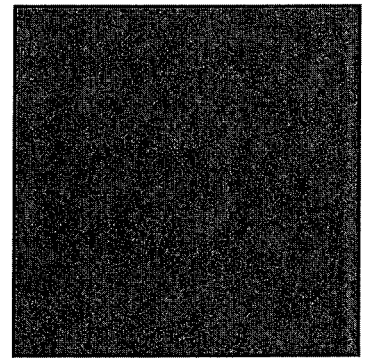
FIG. 4A is a diagram showing a SEM image (full added image) of a surface of the reflective mask.
Figure 4B:
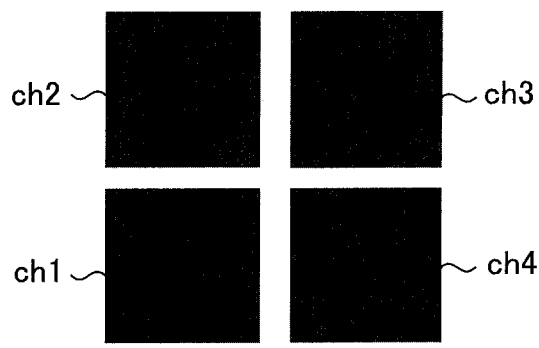
FIG. 4B is a diagram showing SEM images of the respective detector used for generating the SEM image in FIG. 4A.
Figure 4C:
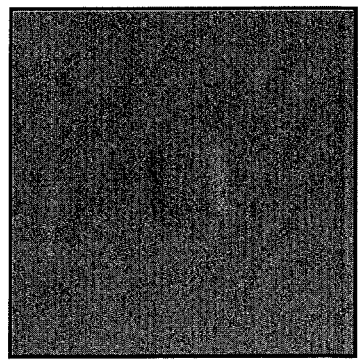
FIG. 4C is a diagram showing a subtracted image obtained by subtracting a right image from a left image.

FIG. 4A is a diagram showing a SEM image (full added image) of a surface of a reflective mask, FIG. 4B is a diagram showing SEM images of the respective detectors used for generating the SEM image in FIG. 4A, and FIG. 4C is a diagram showing a differential image obtained by subtracting a right image from a left image.

The SEM image shown in FIG. 4A is a full added image obtained by adding detection signals of the respective detectors 9a to 9d, and an image is the same as a SEM image obtained by a general scanning electron microscope consisting a single detector. Although a recess-shaped pit defect having a depth of about 14 nm exists in a portion of the surface of the reflective mask corresponding to the shown SEM image, the pit defect does not appear in the SEM image. This result shows that it is difficult to detect minute defects in reflective masks using the general scanning electron microscope.

FIG. 4B is a diagram showing SEM images of the detection signals ch1 to ch4 obtained by the respective detectors 9a to 9d of the defect inspection apparatus 100

In the SEM images shown in FIG. 4B, variations in luminance value appear at a riser portions of a pit defect. To obtain an image in which the irregularities of the pit defect are further emphasized, a subtracted image is obtained by finding a difference between a left image, which is obtained by adding the detection signal ch1 and the detection signal ch2, and a right image, which is obtained by adding the detection signal ch1 and the detection signal ch4.

FIG. 4C is a diagram showing a subtracted image obtained by finding a difference between the left image and the right image.

As shown in FIG. 4C, in the subtracted image, the pit defect appears, which does not appear in the full added image. In this way, the subtracted image obtained by the defect inspection apparatus 100 is suitable for detecting defects arising from minute irregularities.

Next, a much finer defect is observed using the defect inspection apparatus 100 in FIG. 1.

Figure 5:
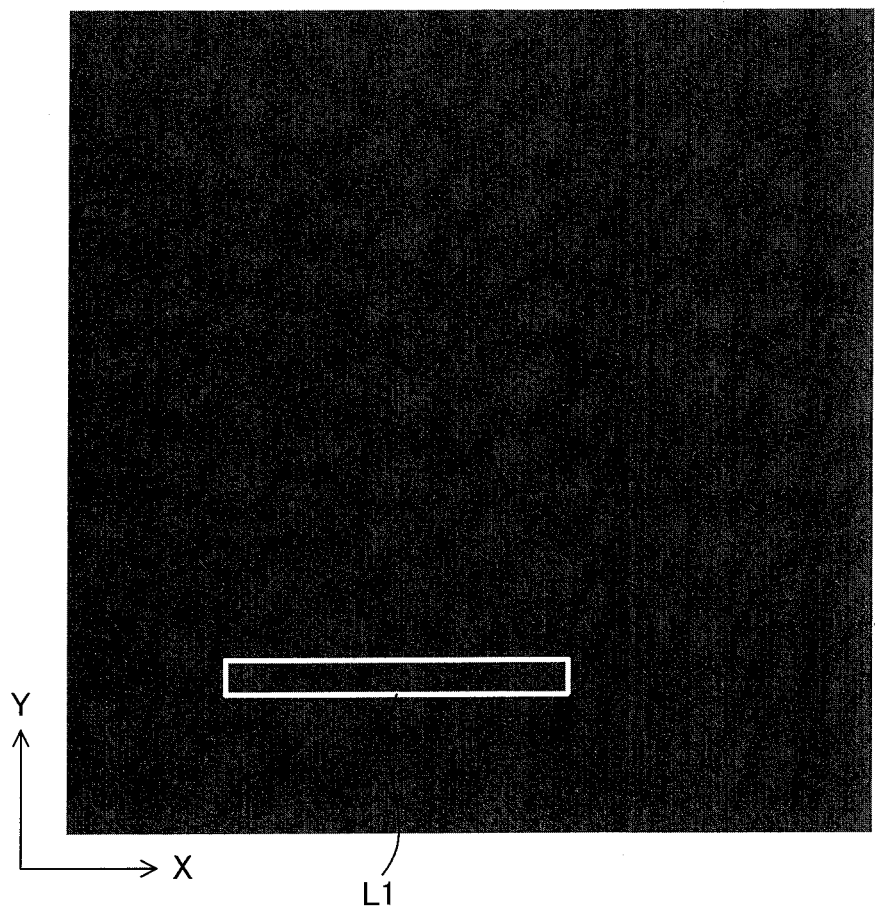
FIG. 5 is a diagram showing a SEM image (subtracted image) of a surface of a sample with a low projection.

FIG. 5 is a diagram showing a differential image of a surface of a sample in which a projection-shaped bump defect is formed.

Here, the observation is performed on a sample with a projection-shaped bump defect having a height of approximately 2 nm and a sample with a projection-shaped bump defect having a height of approximately 1 nm. Note that the subtracted image in FIG. 5 is generated from SEM images captured under conditions where an acceleration voltage of the electron beam is 900 V, a current value was 5 pA, an image resolution is 1024 pixels, an average number is 64, and a scanning speed was 20 MHz.

As shown in FIG. 5, as for the bump defect having a height of approximately 2 nm, the bump defect does not appear even in the subtracted image. In view of this, a line profile of a region L1 extending across the bump defect is extracted from the subtracted image.

Figure 6A:
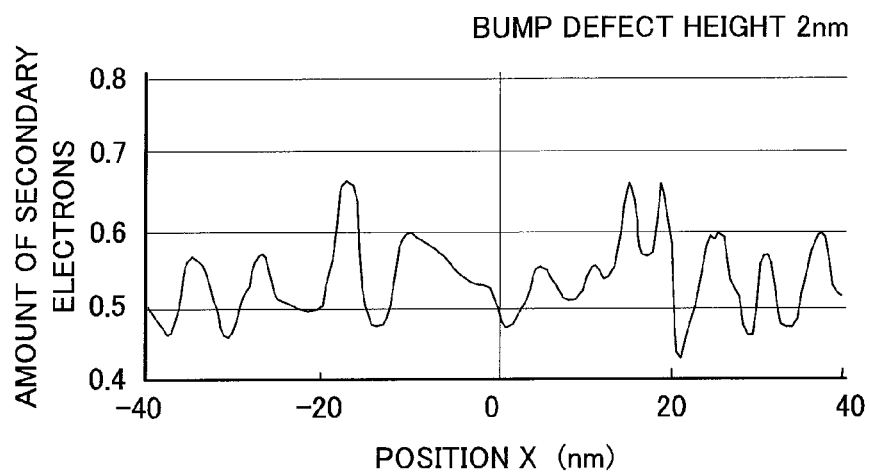
FIG. 6A is a diagram showing an example of a line profile across a projection having a height of 2 nm.
Figure 6B:
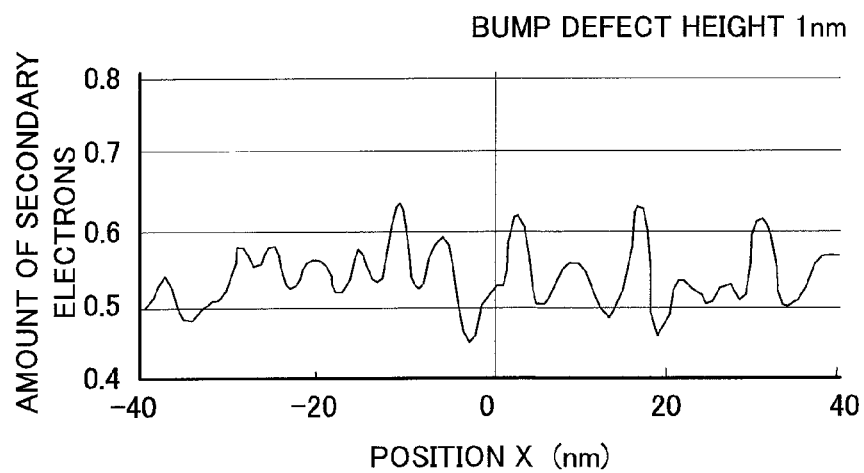
FIG. 6B is a diagram showing an example of a line profile across a projection having a height of 1 nm.

FIG. 6A is a diagram showing an example of a line profile across a projection having a height of 2 nm, and FIG. 6B is a diagram showing an example of a line profile across a projection having a height of 1 nm.

As shown in FIGS. 6A and 6B, when the height or depth of the defect becomes as small as about 2 nm, the peak of the riser portion of the defect is buried in noise components, making it difficult to detect the defect.

In view of this, in the embodiment, with a focus on the fact that the multi-layer reflective film 62 of the EUV mask 60 is made of a conductive material, such as a metal, and thus tends not to cause a charge-up phenomenon, a surface of a sample is observed with a reduced scanning speed of an electron beam.

Figure 7:
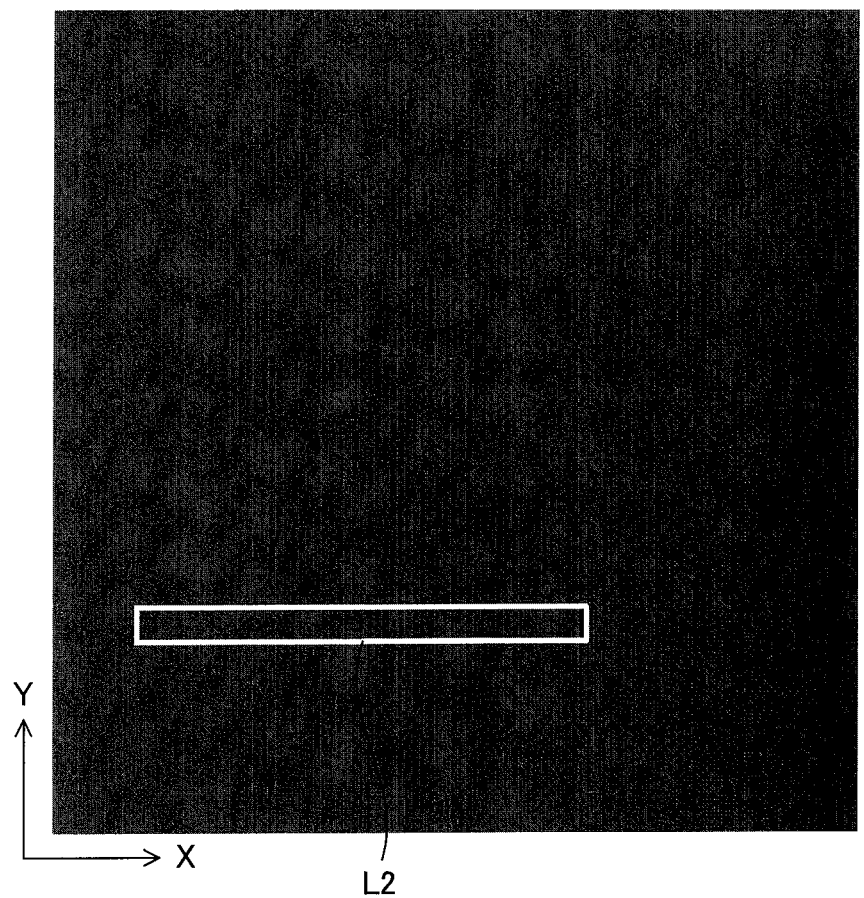
FIG. 7 is a diagram showing a SEM image (subtracted image) of a surface of a sample, which is acquired with a reduced scanning speed of an electron beam.

FIG. 7 is a diagram showing a SEM image (subtracted image) of a surface of a sample acquired with a reduced scanning speed of an electron beam. Note that the subtracted image in FIG. 7 is based on a SEM image captured under the conditions where the acceleration voltage of the electron beam is 900 V, the current value is 5 pA, the image resolution is 1024 pixels, the average number is one, and the scanning speed is 7 kHz.

As shown in FIG. 7, when the scanning speed of the electron beam is set at 1/1000 or less of the scanning speed in the measurement shown in FIG. 5, noise in the subtracted image is reduced, causing luminance variation to appear at the riser portion of the projection-shaped bump defect. Under this condition, a line profile of a region L2 containing a bump defect is extracted.

Figure 8A:
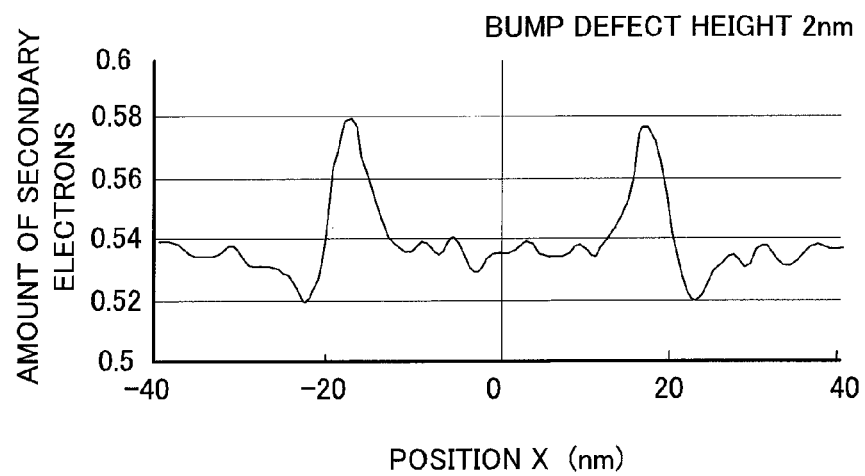
FIGS. 8A and 8B are diagrams showing line profiles obtained from SEM images obtained with a reduced scanning speed of the electron beam.
Figure 8B:
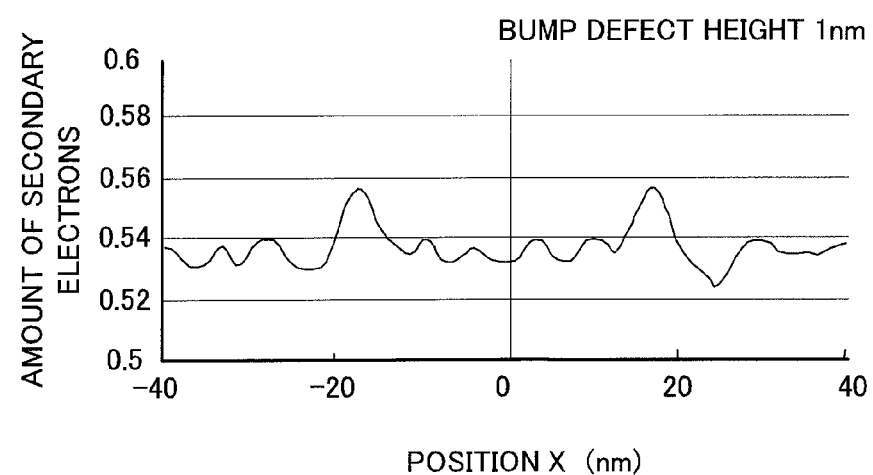

FIG. 8A is a diagram showing a line profile of a bump defect having a height of approximately 2 nm, and FIG. 8B is a diagram showing a line profile of a bump defect having a height of approximately 1 nm.

As shown in FIG. 8A and FIG. 8B, when the scanning speed of the electron beam is reduced to 7 kHz, noise components are reduced as compared to the cases of FIGS. 6A and 6B, and accordingly, a bump defect having a height of 1 to 2 nm may be detected.

As described above, in the embodiment, with a focus on the fact that since the EUV mask is covered with a conductive material, charge may be effectively removed into the surrounding even when an increased number of electrons are irradiated by scanning with the scanning speed of the electron beam set at 7 kHz. In this way, the number of electrons with which the surface of the sample is irradiated increases and the contrast of the defect arising from irregularities are improved, therby making it possible to detect such defect arising from minute irregularities.

Note that, the observation method according to the embodiment is not limited to the observation of an EUV mask, but may be employed for observation of minute irregularities on a surface of any sample covered with a conductive material.

Hereinafter, procedures of the defect inspection method of the embodiment from detection of a defect arising from irregularities to measurement of the width and the depth of the defect will be described.

Figure 9:
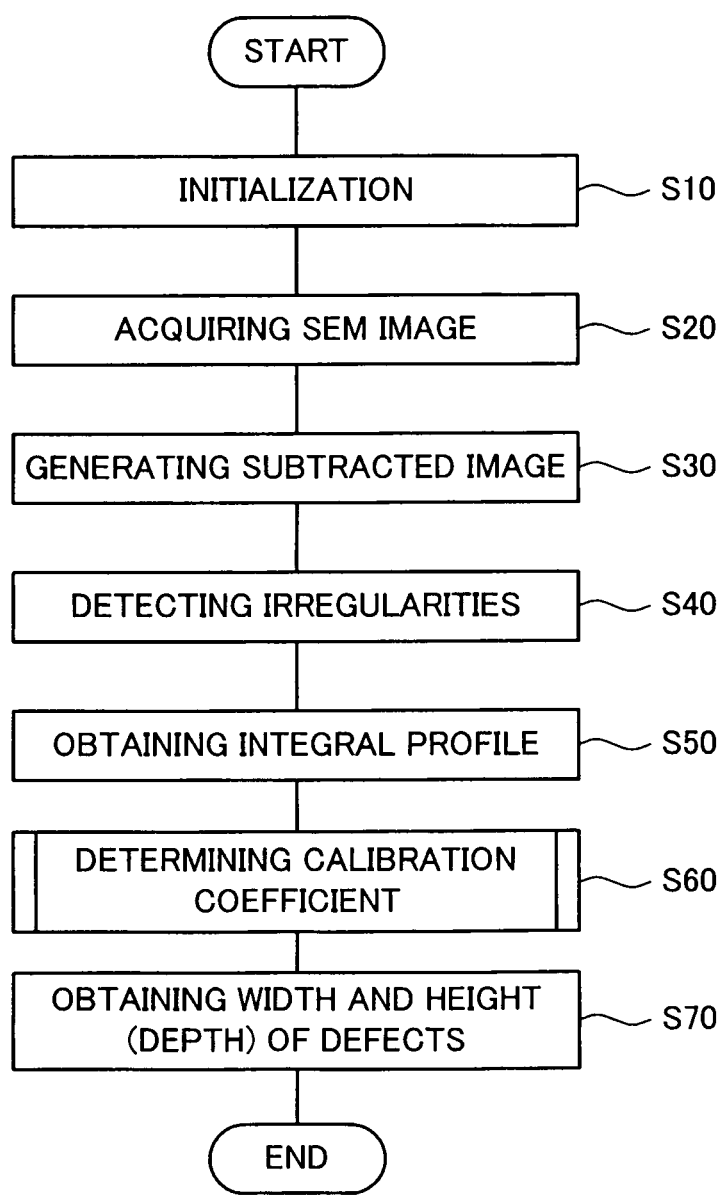
FIG. 9 is a flowchart showing a defect inspection method according to the embodiment.

FIG. 9 is a flowchart showing the defect inspection method according to the embodiment.

First, in Step S10 in FIG. 9, the control unit 10 of the defect inspection apparatus 100 (see FIG. 1) initializes the acceleration voltage, the current value, and the scanning speed of the electron beam.

In the embodiment, the acceleration voltage is preferably set as low as possible in order to detect minute irregularities. For example, it is preferable that the acceleration voltage be set at 1 kV or lower. In addition, from the viewpoint of reducing noise components, the amount of the electron beam irradiated is preferably increased in the case of a sample covered with a conductive material. For example, it is preferable that the current value of the electron beam be set at 5 pA or higher and the scanning speed of the electron beam be set at 20 kHz or lower.

Next, in Step S20, a SEM image of the surface of the sample is acquired by the defect inspection apparatus 100.

Here, the signal processing unit 11 generates SEM images for the detection signals ch1 to ch4 from the respective detectors 9a to 9d, a left image obtained by adding the detection signals ch1 and ch2, and a right image obtained by adding the detection signals ch3 and ch4.

Next, in Step S30, the analysis unit 12 of the defect inspection apparatus 100 generates a subtracted image by finding a difference between the left image and the right image. The luminance of the subtracted image is a value corresponding to the inclination of the surface of the sample. For this reason, one of the inclined side of the irregularities appears with a higher luminance than that of the flat portion, and the other inclined side appears darker with a lower luminance than that of the flat portion.

Next, in Step S40, the analysis unit 12 detects the position of the irregularities (defect) based on the presence of a portion where the luminance value of the subtracted image changes by a predetermined threshold or more.

Next, in Step S50, the analysis unit 12 extracts a line profile (subtraction profile) of the subtracted image. Note that it is preferable that the subtraction profile is extracted along a line parallel to the direction in which the difference is determined.

Subsequently, the subtraction profile is added to obtain an integral profile, which is a distribution of added value. Thus, the integral profile obtained by adding the subtraction profile representing a distribution in inclination of the surface of the sample reproduces a distribution in height of a pattern and a defect on the sample surface.

It should be noted however that since the scanning speed of the electron beam is set low in the embodiment for increasing the amount of electrons in the irradiation, which tends to change the electrical potential at the surface of the sample while the scanning is performed. Accordingly, unevenness in luminance is formed in the acquired SEM image (subtracted image), leading to a phenomenon in which the luminance value varies depending on the position in the image.

As a result, a large deformation is formed in the integral profile obtained by adding the subtracted signal, causing a problem that disagreement of the integral profile occurs with the actual shape of the pattern and defect.

In view of this, in the embodiment, the integral profile is calibrated in accordance with a method as described below.

Figure 10A:
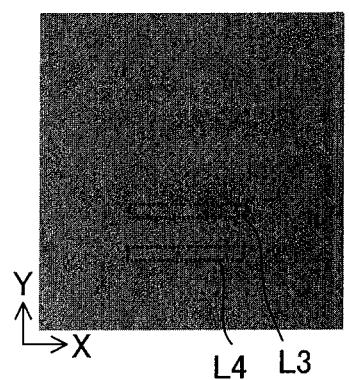
FIGS. 10A to 10C are diagrams showing a method of calculating an integral profile.
Figure 10B:
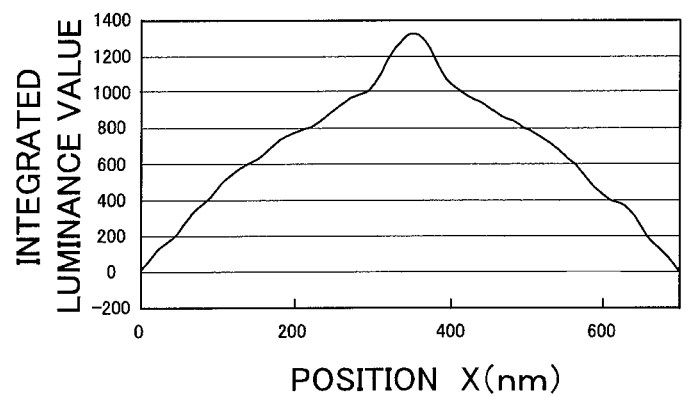
Figure 10C:
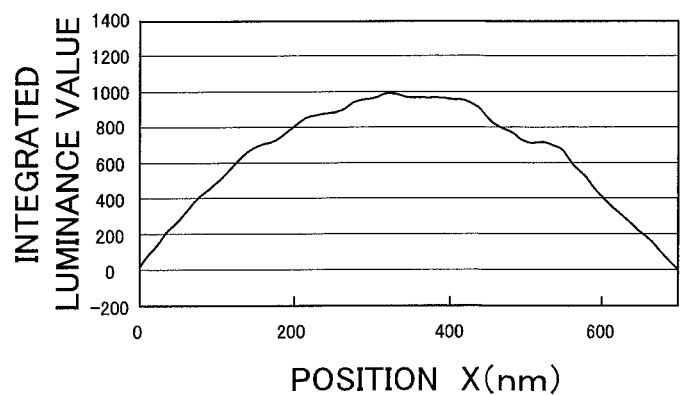

FIGS. 10A to 10C are diagrams showing a method of calculating an integral profile.

FIG. 10A shows a subtracted image generated from a SEM image acquired by scanning of an electron beam at a low speed. As shown in FIG. 10A, there is unevenness in luminance in the subtracted image, such that the luminance is higher (brighter) on the left side edge and lower (darker) on the right side edge. In this manner, the distribution of the unevenness in luminance due to electrification varies only in an X direction, which is the scanning direction of the electron beam, and is substantially constant in a Y direction, which is a direction orthogonal to the scanning direction of the electron beam.

In view of this, a line profile of a luminance value in a region L3 (defect portion) extending horizontally across the defect is first extracted from the subtracted image in FIG. 10A. The line profile is then added to obtain an integral profile of the defect portion.

FIG. 10B is a diagram showing the integral profile of the defect portion (the region L3) in FIG. 10A. As shown in FIG. 10B, whole of the integral profile of the defect portion is deformed projecting upward.

Next, a line profile of a luminance value in a region L4 (background portion) which is located at the same position in the X direction as the region L3 without overlapping the defect is extracted from the subtracted image in FIG. 10A. The line profile is then added to obtain an integral profile of the background portion.

FIG. 10C is a diagram showing the integral profile of the background portion (the region L4). As shown in FIG. 10C, whole of the integral profile of the background portion is also deformed projecting upward.

Next, the integral profile of the background portion is subtracted from the integral profile of the defect portion.

Figure 11:
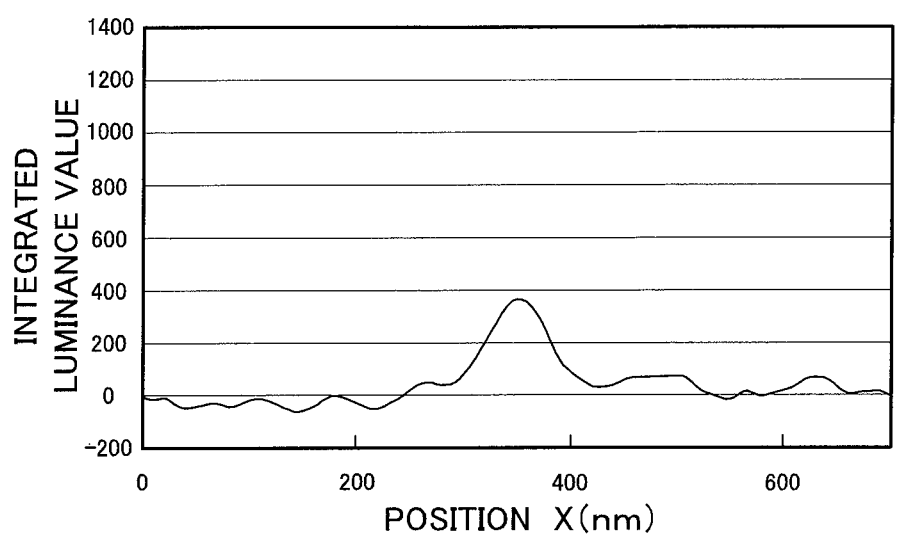
FIG. 11 is a diagram showing an integral profile obtained by subtracting an integral profile in FIG. 10C from an integral profile in FIG. 10B.

FIG. 11 is a diagram showing a result of subtracting the integral profile in FIG. 10C from the integral profile in FIG. 10B.

In this way, an integral profile of the defect portion with the integral profile of the deformation being removed is obtained. In the integral profile thus calibrated, an influence of the unevenness in luminance is counterbalanced, and the distribution in height of the defect may accurately be reproduced.

Next, in Step S60 in FIG. 9, the analysis unit 12 (see FIG. 1) determines a calibration coefficient for determining the height (depth) of the defect from the integral profile.

The value of the integral profile obtained in Step S50 described above is a luminance value. To obtain the heights of the pattern or the defect from this luminance value, it is necessary to covert the luminance value to a value in length by multiplying a scale value of the subtracted image and a certain calibration coefficient together. This calibration coefficient depends on the emission characteristic of secondary electrons, which relates to the material of the sample irradiated with the electron beam.

Accordingly, the calibration coefficient is constant when the material and the structure of the EUV mask to be measured is the same.

However, the signal intensity of secondary electrons varies also due to the acceleration voltage, the current value, and the number of scanning by the electron beam of the defect inspection apparatus 100, as well as the contrast of an image. Accordingly, the calibration coefficient varies also due to the measurement conditions.

In view of this, in the embodiment, the calibration coefficient is determined in accordance with an approach as described below.

Figure 12:
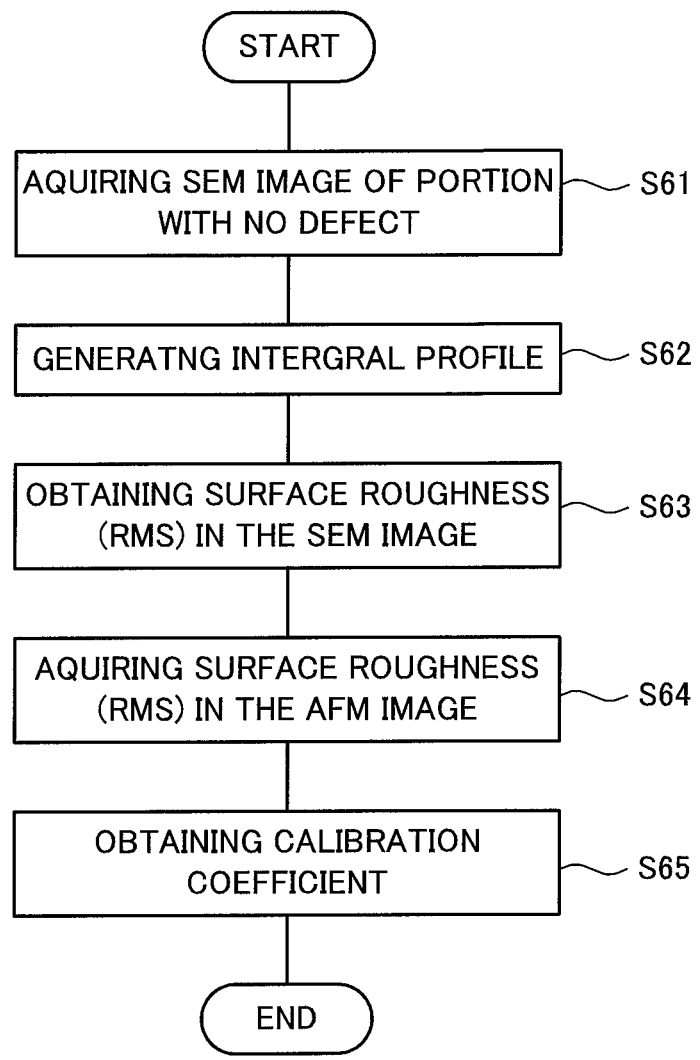
FIG. 12 is a flowchart showing a method of determining a calibration coefficient.

FIG. 12 is a flowchart showing a method of determining a calibration coefficient according to the embodiment.

First, in Step S61 in FIG. 12, an observation region is set in a portion of the sample where no defect exists, and a SEM image of the observation region is acquired by the defect inspection apparatus 100. This SEM image is captured with the same acceleration voltage, the same current value, the same number of scanning, and the same scanning speed of the electron beam as those adopted in the observation of a defect.

Next, in Step S62, the analysis unit 12 generates a subtracted image from the SEM image acquired in Step S61, and adds a line profile of luminance of the subtracted image to acquire an integral profile.

Figure 13A:
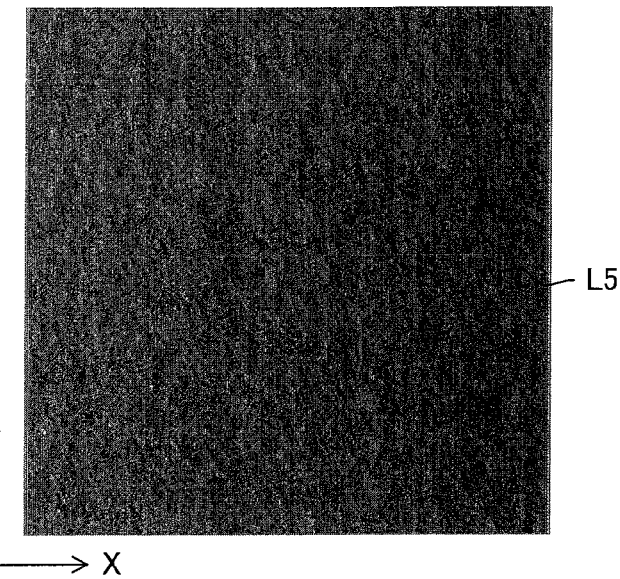
FIG. 13A is a diagram showing how an average surface roughness is found from an SEM image of a portion with no defect.

FIG. 13A shows an example of a subtracted image of a portion with no defect. In the case of FIG. 13A, the integral profile is obtained from a line profile of a region L5 in the middle of the Y direction.

In this way, a distribution in height of the portion with no defect is reproduced.

Next, in Step S63 in FIG. 11, the analysis unit 12 obtains data of the luminance value of the integral profile acquired in Step S62 multiplied by a scale of the subtracted image. The analysis unit 12 then obtains an RMS (Root Mean Square) value of a surface roughness in the SEM image from the data obtained by multiplying the integral profile and the scale of the subtracted image together.

Figure 13B:
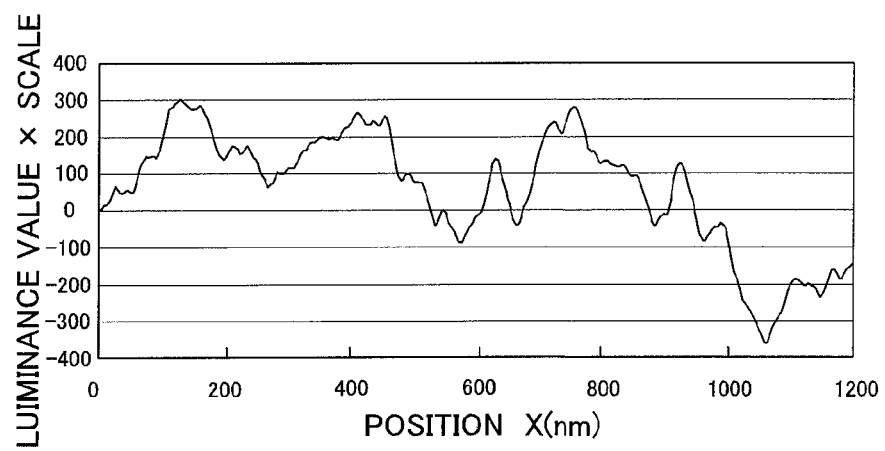
FIG. 13B is a graph showing the data obtained by multiplying the integral profile acquired from FIG. 13A and the scale of the subtracted image together.

FIG. 13B is a graph showing the data obtained by multiplying the integral profile acquired from FIG. 13A and the scale of the subtracted image together.

In the case of FIG. 13B, the obtained surface roughness of the sample in FIG. 13A is 167.8.

Next, in Step S64 in FIG. 12, the analysis unit 12 acquires the surface roughness (RMS) of the surface of the sample, which is measured in advance using an atomic force microscope (AFM) of the region as the observation region set in Step S61.

Note that in the case where the sample is an EUV mask commercially available as a product, the surface roughness (RMS) of the EUV mask depends on the manufacturer and the product grade. For this reason, when the same product is used, the measurement using the atomic force microscope is not necessary every time, and the value of the surface roughness (RMS) needs only to be measured in advance.

Next, in Step S65, a calibration coefficient K is obtained such that the surface roughness in the SEM image is consistent with the surface roughness obtained by the AFM. Specifically, the calibration coefficient K is obtained by dividing the surface roughness (RMS) obtained by the AFM with the surface roughness (RMS) in the SEM image.

In the case of the sample in FIG. 13A, since the surface roughness (RMS) obtained by the AFM is 0.3 (nm), the calibration coefficient K of this sample is 0.3/167.8=0.001788.

Thus, the calibration coefficient for obtaining the height (depth) of a defect from the luminance value of the integral profile is obtained.

Next, in Step S70 in FIG. 9, the analysis unit 12 (see FIG. 1) obtains the height (depth) of the defect and the width of the defect based on the integral profile.

Figure 14:
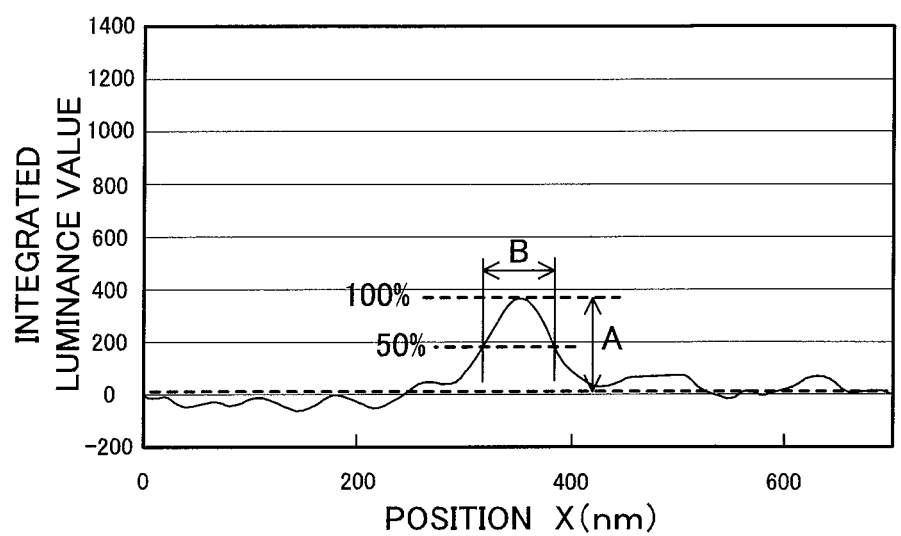
FIG. 14 is a diagram showing a method of finding a pattern width and a pattern height (depth) from an integral profile; and, FIGS. 15A and 15B are graphs showing results of examining heights (depths) of defects detected with a normal scan and a slow scan.

FIG. 14 is a graph showing a method of obtaining a pattern width and a pattern height (depth) from the integral profile.

The height (depth) and width of the defect is obtained in the following way.

First, as shown in the integral profile in FIG. 14, a difference A between an average value of luminance values of flat portions (0%) which the peak of the defect excluded and the luminance value of the peak of the defect (100%) is obtained.

Next, the difference A in luminance value is multiplied by the calibration coefficient obtained in Step S60. In this multiplication, the height of the defect is obtained.

In addition, to detect the width of the defect, a threshold is set at a luminance value of 50% between the luminance value of the flat portions (0%) and the peak of the defect (100%), and portions where the integral profile and the threshold intersect with each other are detected as endpoints for the defect. The width of the defect may be obtained from a distance B between the endpoints of the defect thus detected.

As described above, the defect inspection method according to the embodiment may detect a defect formed of minute irregularities by low speed scanning of an electron beam, and further may accurately measure the height (depth) and width of the defect.

EXAMPLES

Hereinafter, results of evaluation will be described, where EUV masks having bump defects and pit defects having various heights (depths) and widths are prepared to evaluate the detectable heights (depths) of defects.

FIG. 15A is a graph showing results of detecting defects according to Example 1 of the embodiment.

In Example 1, SEM images are captured under conditions where an electron beam is set at the acceleration voltage of 900 V, the current value of 5 pA, and the number of scanning is set at one. Note that, in a normal scanning condition, the scanning speed of the electron beam is set at 20 MHz, whereas in a slow scanning condition, the scanning speed of the electron beam is set at 7 kHz.

As shown in FIG. 15A, it is confirmed that capturing SEM images with the slow scan makes it possible to detect defects in a range down to about 2 nm which are difficult to detect with the normal scan.

FIG. 15B is a graph showing results of detecting defects according to Example 2 of the embodiment.

In Example 2 SEM images are acquired under conditions where an electron beam is set at the acceleration voltage of 500 V, the current value of 12 pA, and the number of scanning is set at one. Note that in the normal scanning, the SEM images are acquired under a condition where the scanning speed of the electron beam is set at 20 MHz, and in the slow scanning, the SEM images are acquired under a condition where the scanning speed of the electron beam is set at 7 kHz.

As shown in FIG. 15B, it is confirmed that defects of more minute irregularities may be detected by decreasing the acceleration voltage and increasing the current value of the electron beam.

It is confirmed that defects formed of irregularities of about 1 nm to 2 nm, which are difficult to detect with the normal scan, may be detected by performing the slow scanning as shown in FIGS. 15A and 15B.

What is claimed is:
1. A defect inspection apparatus comprising:
   an electron scanning unit configured to scan a surface of a sample with an electron beam;
   a plurality of detectors arranged around an optical axis of the electron beam and configured to detect electrons emitted from the surface of the sample by scanning with the electron beam;

a signal processing unit configured to generate image data of the surface of the sample based on detection signals from the detectors;

an analysis unit configured to detect a defect due to irregularities of the surface of the sample based on the image data;

a control unit configured to control a scanning speed of the electron beam depending on the type of the sample, wherein the signal processing unit generates a subtracted image obtained by subtracting an image data captured for a first direction from another image captured for a second direction opposite to the first direction with an optical axis of the electron beam in-between, wherein the analysis unit detects the irregularities of the surface of the sample based on a luminance value of the subtracted image, wherein the analysis unit calculates subtraction profiles of a defect portion containing the irregularities and a background portion where the irregularities are not detected respectively in the subtracted image, and wherein the analysis unit finds an integral profile by subtracting a background integral profile obtained by adding the subtraction profile of the background portion from a defect integral profile obtained by adding the subtraction profile of the defect portion.

2. The defect inspection apparatus according to claim 1, wherein when the sample is a reflective mask formed of a conductive material, the control unit sets the scanning speed of the electron beam lower than the scanning speed used when the sample is a transmissive mask with a pattern formed on a substrate formed of an insulating material.

3. The defect inspection apparatus according to claim 1, wherein the analysis unit finds a height of the defect from a luminance value of the integral profile based on a relation between a value of a surface roughness obtained from the integral profile and a value of a surface roughness of the sample obtained using an atomic force microscope.

4. The defect inspection apparatus according to claim 2, wherein when the sample is a reflective mask formed of a conductive material, the control unit sets the scanning speed of the electron beam at 1/1000 or less of the scanning speed used when the sample is a transmissive mask with a pattern formed on a substrate formed of an insulating material.

5. A defect inspection method using a defect inspection apparatus including an electron scanning unit configured to scan a surface of a sample with an electron beam, a plurality of detectors arranged around an optical axis of the electron beam and configured to detect electrons emitted from the surface of the sample by irradiation with the electron beam, and a control unit configured to control the electron scanning unit, the method comprising:

determining a scanning speed of the electron beam depending on the type of the sample;

scanning the electron beam and acquiring a plurality of image data of the surface of the sample captured in different directions based on detection signals of the detectors;

generating a subtracted image by subtracting an image data captured for a first direction from another image data captured for a second direction opposite to the first direction with an optical axis of the electron beam in-between;

extracting a subtraction profile from the subtracted image and detecting irregularities of the surface of the sample based on the subtraction profile, calculating subtraction profiles of a defect portion containing the irregularities and a background portion where the irregularities are not detected respectively in the subtracted image, and finding an integral profile by subtracting a background integral profile obtained by adding the subtraction profile of the background portion from a defect integral profile obtained by adding the subtraction profile of the defect portion.

6. The defect inspection method according to claim 5, wherein when the sample is a reflective mask formed of a conductive material, the scanning speed of the electron beam is set lower than the scanning speed used when the sample is a transmissive mask with a pattern formed on a substrate formed of an insulating material.

7. The defect inspection method according to claim 5, further comprising:

finding a height of the defect from a luminance value of the integral profile based on a relation between a value of a surface roughness obtained from the integral profile and a value of a surface roughness of the sample obtained using an atomic force microscope.

8. The defect inspection method according to claim 6, wherein when the sample is a reflective mask formed of a conductive material, the scanning speed of the electron beam is set at 1/1000 or less of the scanning speed used when the sample is a transmissive mask with a pattern formed on a substrate formed of an insulating material.

* * * * *